US005693614A

United States Patent [19]
Torii et al.

[11] Patent Number: 5,693,614
[45] Date of Patent: Dec. 2, 1997

[54] DRUG FOR THE TREATMENT OF SENILE DEMENTIA OF THE ISCHEMIC AND HYPOGLYCEMIC TYPES

[75] Inventors: Kunio Torii, Kawasaki; Yutaka Oomura, Shuita; Kazuo Sasaki, Toyama; Hiroyuki Kojima, Kawasaki, all of Japan

[73] Assignee: Ajinomoto Co., Inc., Toyko, Japan

[21] Appl. No.: 261,050

[22] Filed: Jun. 14, 1994

Related U.S. Application Data

[63] Continuation of Ser. No. 873,682, Apr. 24, 1992, abandoned, which is a continuation of Ser. No. 494,425, Mar. 16, 1990, abandoned.

[30] Foreign Application Priority Data

Mar. 16, 1989 [JP] Japan ................................ 1-064057

[51] Int. Cl.$^6$ .......................... A61K 37/02; A61K 37/36; C07G 7/00
[52] U.S. Cl. ........................ 514/12; 514/21; 530/350; 530/399
[58] Field of Search .................... 514/12, 21; 530/399, 530/350

[56] References Cited

U.S. PATENT DOCUMENTS

| | | | |
|---|---|---|---|
| 4,296,100 | 10/1981 | Franco | 514/21 |
| 4,378,347 | 3/1983 | Franco | 514/12 |
| 4,444,760 | 4/1984 | Thomas, Jr. | 530/399 |
| 4,923,696 | 5/1990 | Appel | 530/350 |
| 5,057,494 | 10/1991 | Sheffield | 514/12 |

FOREIGN PATENT DOCUMENTS

WO8503869 9/1985 WIPO.

OTHER PUBLICATIONS

Research Communications in Psychology, Psychiarty & Behavior, vol. 12, No. 2, 1987, pp. 105–117, H. Laborit, et al., "Phorbol Esters Antagonize Scopolamine–Induced Amnesia of a Passive Avoidance".

Journal De Physiologie, vol. 81, No. 4, 1986, pp. 252–260, D.L. Alkon, et al., "Biochemical Mechanisms of Memory Storage".

Neurobiology of Aging, vol. 11, No. 1, Jan./Feb. 1990, p. 77, J.R. Connor, "Iron Storage and Transport Proteins in the Brain in Aging and Alzheimer's Disease".

Nature, vol. 332, No. 6162, Mar. 24, 1988, pp. 360–361, K.J. Anderson, et al., "Basic Fibroblast Growth Factor Prevents Death of Lesioned Cholinergic Neurons in vivo".

The Merck Index, 11th Edition, 1989, p. 637, Abstract No. 4016, "Fibroblast Growth Factor".

Brain Research, vol. 452, No. 1 & 2, Jun. 14, 1988, pp. 164–174, G. Cole, et al., "Decreased Levels of Protein Kinase C in Alzheimer Brain".

The Canadian Journal of Neurological Sciences, vol. 15, No. 2, May 1988, p. 221, R. Garza, et al., "Influence Des Facteurs Neuronotrophiques Sur La Differenciation Des Neurones Cholinergiques Centraux De Rat En Culture Cellulaire" Translation not supplied.

Illustrated Stedman's Medical Dictionary, 24 Ed. Williams and Wilkins, Baltimore 1982, p. 728.

Walicke, *Experimental Neurology*, 102, 144–148, 1998.

Esch et al., *Biochemical Biophysical Research Communications*, 133, No. 2, 554–562, 1985.

*Primary Examiner*—Howard E. Schain
*Assistant Examiner*—P. Lynn Touzeao
*Attorney, Agent, or Firm*—Oblon, Spivak, McClelland, Maier & Neustadt, P.C.

[57] ABSTRACT

A subject suffering from ischemic shock is treated by administering to the subject a therapeutically effective amount of aFGF as the active ingredient of a pharmaceutical composition further containing a pharmaceutically acceptable carrier.

5 Claims, 7 Drawing Sheets x13.2 x100 x 13.8 x 100

DRUG FOR THE TREATMENT OF SENILE DEMENTIA OF THE ISCHEMIC AND HYPOGLYCEMIC TYPES

This application is a continuation of application Ser. No. 07/873,682 filed on Apr. 24, 1992, now abandoned, which is a CON of 07/494,425 filed Mar. 16, 1990 now abandoned.

BACKGROUND OF THE INVENTION

1. Field of the Invention

The present discovery relates to a drug for the treatment of senile dementia which exhibits little adverse effect.

2. Description of the Background

The proportion of elderly people in Japan is getting higher year by year. The population of people older than 65 years of age is approximately 10.5% of the total. At the beginning of the 21st century, the elderly population level will reach approximately 16% of the total population. As the proportion of aged people increases, the incidence of people with senile dementia could be twice as high as now and the number of patients could reach beyond one and a half million. This number of people is a relatively huge number which could impose a serious burden on families and hospitals and further the treatment of such a number of people could represent a heavy national expenditure which should become worse. The development of an effective therapy for senile dementia is a most important objective in the medical field along with a treatment for cancer and AIDS.

Now, the form of senile dementia which is by far the most common is brain ischemia, which is quite difficult to regress completely by any therapeutic method after the dementia is established. However, the prevention of senile dementia could reduce risk factors, such as brain hemorrhaging and any obstacles of blood flow. In addition, brain hypoxia after carbon monoxide intoxication, heart shock, severe hemorrhaging, or the failure of energy metabolism in the brain because of hypoglycemia or prolonged seizure are also risk factors which cause dementia.

The prevention of senile dementia, which develops by brain damage after brain ischemia and hypoglycemia, requires not only the suppression of neuronal death but also the induction of plasticity and reconstruction of the neuronal network by remaining intact neurons.

The brain, which is only about 2% of the body weight, requires about 15% of the cardiac output, as well as 20% of the total amount of oxygen consumed by the body.

The source of energy in the brain is the aerobic oxidation of glucose which is supplied by the peripheral blood stream. The brain consumes 25% of the total glucose expenditure. It is significant that both the oxygen and glucose which are necessary for brain energy expenditure are difficult to store. Further, either energy metabolism or physiological function of the brain stops several dozens of seconds after the Supply of energy is terminated. Still further, if the disruption of energy source supply to the brain is prolonged, irreversible brain damage likely occurs.

These facts clearly indicate that the brain as a very valuable organ, dysfunctions with inadequate energy metabolism. A similar pattern of brain damage is also likely to occur in cases of brain hypoxia, ischemic hypoglycemia and continuous seizure. Accompanying brain damage is necrosis of neurons which is induced presumably by the extraordinary release of excitatory neurotransmitters extracellularly such as glutamic and aspartic acids.

Recently, several antagonists for these excitatory neurotransmitters have been developed to prevent brain damage after spasms, but their pharmaceutical efficacy is still inadequate to suppress brain dysfunction including dementia.

Major pathological changes in gerbils after ischemic treatment is neuronal death (necrosis), which is distributed specifically, in terms of the selective vulnerability of the hippocampus in the CA1 layer. Purkinje's cells of the cerebellum, the lateral area of the corpus striatum, the 3rd, 5th, and 6th layers of the cerebrum cortex (Kirino, T.: Brain Res., 239, 57. (1982) etc.) and especially the hippocampus, which is composed of the dentate gyrus and, the CA3 and CA1 layers, seem to play some important roles both in the acquisition of memory and in the recognition of new information.

When the blood flow becomes normal following ischemic treatment by the occlusion of the bilateral carotid artery for a short term, the homeostasis and energy metabolism in the brain, including the hippocampus, are easily reestablished nutritionally and physiologically concurrently with the normal action potential of the pyramidal cells in the hippocampus (Monnghan, D. H., et al: Nature, 306, 176 (1983)). Nonetheless, the pyramidal cells exhibit necrosis from 3 to 4 days after the ischemic treatment despite no lesions both of the grial cells and dendrites which project into the CA1 layer (Petito, C. K. et al.: Neurology, 37, 1281 (1987)). This phenomenon is able to explain the markedly enhanced level of glutamic acid as an excitatory L-amino acid extracellularly by its higher release and lower uptake after a prolonged ischemic condition, which causes extraordinary excitation of neurons, then, an influx of extracellular Ca ion degradation of lipid and protein intracellularly, and finally the neurons die by dysfunction and damage of mitochondria (Benveniste, H. et al.: J. Neurochem, 43, 1369, (1984), Duce, I. R. et al.: Brain Res, 263, 77 (1983)). A need therefore continues to exist for an improved method of treating senile dementia.

SUMMARY OF THE INVENTION

Accordingly, one object of the present invention is to provide a drug for the treatment of senile dementia, which does not exhibit any adverse effect, in terms of tolerance of the neurons to highly enhanced glutamic acid levels extracellularly, of suppression of the neuronal death rate and of the reconstruction of the neuronal network by the introduction of plasticity during and after the ischemic condition in the brain and which is effective immediately upon administration and after repeated administrations.

Briefly, this object and other objects of the present invention as hereinafter will become more apparent can be attained with a pharmaceutical composition effective for the treatment of senile dementia which comprises a therapeutically effect amount of αFGF active substance in combination with a pharmaceutically acceptable carrier.

BRIEF DESCRIPTION OF THE DRAWINGS

A more complete appreciation of the invention and many of the attendant advantages thereof will be readily obtained as the same becomes better understood by references to the following detailed description when considered in connection with the accompanying drawings, wherein.

DETAILED DESCRIPTION OF THE PREFERRED EMBODIMENTS

The most vulnerable area of neuronal death in the brain is in the pyramidal cells in the CA1 layer of the hippocampus after brain ischemia and hypoglycemia.

When experimental animals exhibiting fore brain ischemia received treatment with the drug of the present invention, normal blood flow was quickly restored, i.e., gerbils, in 5 minutes and is 10 to 30 minutes for rats. Blood flow reached normal levels after the termination of the bilateral occlusion of the carotid artery. In the tests gerbils were treated for only five minutes while rats were treated for 10 to 30 minutes and improvement was noted.

Both the content of ATP and the energy charge level in the brain as parameters of energy metabolism declined rapidly during brain ischemia and recovered very soon after the treatment terminated. There are no pathological changes of the pyramidal cells in the hippocampal CA1 layer until 24 hours after brain ischemia. Additionally, it is possible to record the electrical activity of these neurons, which impulse per second intracellularly increases rather than that in intact animals. These data suggest that the pyramidal cells in the hippocampal CA1 layer are still alive at least until the first day, but these neurons lose electrophysiological responses and fall in the state of functional death at the second day after treatment. Three or four days later, after the short term brain ischemia, the pyramidal cells in the hippocampal CA1 layer exhibit almost complete necrosis.

The development of this brain lesion gradually progresses as so-called "delayed neuronal death" rather than the brain damage as caused by glutamic acid agonist, i.e., kinic acid. Both anemic and hemorrhagic infarcts in the brain, induced by brain thrombosis, carbon monoxide intoxication, heart shock, severe hemorrhaging and so on, are sufficiently potent to cause ischemic brain damage. Also the failure of energy metabolism in the brain resulting from hypoglycemia, prolonged seizure, i.e., epilepsy, elicits this type of lesion formation. In these cases, either the tolerance to excessive glutamic acid extracellularly or the maintenance of brain homeostasis by effective drugs tends to suppress the development of brain damage and consequently prevents dementia.

In any event, the tremendously high concentrations of glutamic acid and the consequent histological damage to the brain after brain ischemia never occur in ordinary life, even when people have high protein diets which contain large amounts of glutamic acid.

Figure 1:
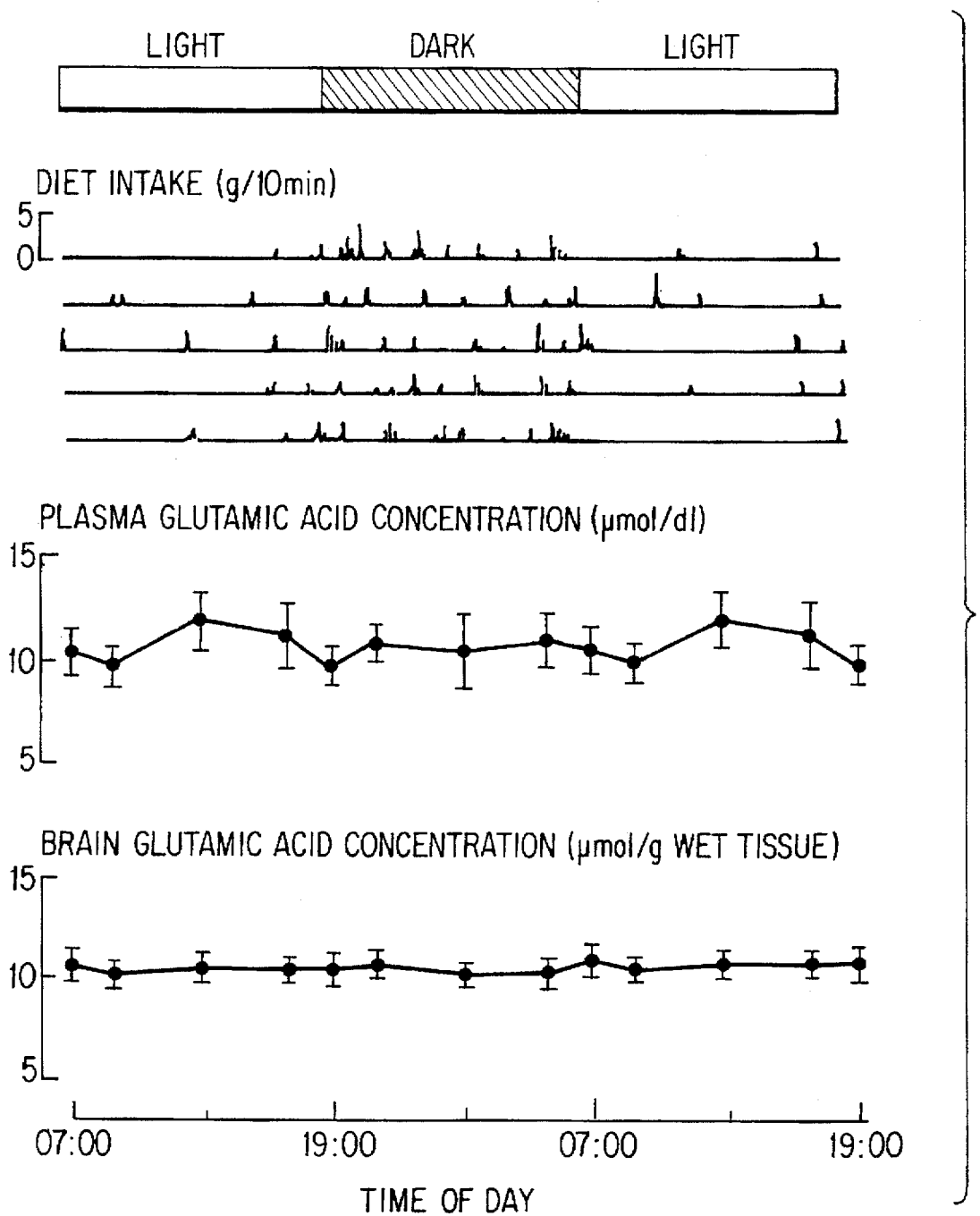
FIG. 1 shows the Circadian variation of feeding male rats and the glutamic acid concentration in the plasma and in the brains of the rats.

FIG. 1 is a typical diagram showing the Circadian rhythm of glutamic acid in plasma and the brain, concurrent with an intake of a diet containing 6.8% (w/w) of L-glutamic acid as protein source, in male Sprague-Dawley strain rats (N=8), weighing 350 g. These data indicate that glutamic acid level in plasma, as well as in the brain remain unchanged when large amounts of glutamic and aspartic acids are ingested during both digestion and absorption phases.

In addition to this data, it has been reported that the plasma and brain levels of glutamic acid never increase, when mice are fed a diet to which is added 30% (w/w) monosodium glutamate. Further, the placental transfer of increments of glutamic acid, present in mother milk, are not recognized even in cases where the plasma glutamic acid in dams is experimentally high.

These phenomena are quite explainable on the basis that the plasma and, especially, brain glutamic acid levels remain essentially unchanged when major amounts of glutamate are absorbed because of catabolism of glutamic acid into alanine and/or glutamine. Further, the barrier systems of the alimentary organs, brain, placenta and mammary gland need to function well.

In contrast, when infant mice, 9 or 10 days of age, received an excessive dose of L-glutamate (i.e., 4 g/kg body weight) parenterally or by forced intubation with a concentrated solution, their plasma level, as well as brain level of glutamic acid increased several hundred times higher than normal and caused forced necrosis in the vulnerable area of the brain, i.e., the hippocampus substantial nigra, area postrama, amygdala, olfactory bulb, and hypothalamus (the paraventricular nuclei, the arcuate nuclei, the median eminence), because the barrier systems of the infant mice to an experimentally severe loading of glutamic acid is still immature and unable to sufficiently operate.

On the other hand, brain lesions in the mice were severely suppressed when infant mice were pre-treated with certain nutrients orally such as by milk formulas or its ingredients (glucose or L-amino acids), one hour prior to the severe loading of L-glutamic acid experimentally. Of course, plasma glutamic acid levels are remarkably enhanced by this treatment. It is believed that these results are attributable to the cephalic phase, both olfactory and gastatory stimuli, subsequent absorption of nutrients from the alimentary tracts along with secretion of humoral factors such as gastrointestinal hormones and growth factors to be neurotrophic. The factors enhance the survival rate of neurons at higher concentrations of glutamic acid in the brain beyond physiological limits.

It has been discovered that neurotrophic changes occur during, as well as after meal time. One change is a several thousand fold increase from normal levels of acidic fibroblast growth factor (aFGF) at about one and one-half hour after a meal. Another change is that the platelet derived growth factor (PDGF) declines to levels of about one-eighth the normal level.

It is known that the sprouting of neurites is elicited when both growth factors are added to a culture medium. Furthermore, when the effects of aFGF and PDGF at very low dosages, on the potency of anorexigenic functions are examined, aFGF alone was sufficiently potent to decrease the diet intake and to cause spontaneous discharge of glucose sensitive neurons in the lateral hypothalamic area (feeding center) into rats, which were administered αFGF in the brain (FIGS. 2 and 3).

Figure 2:
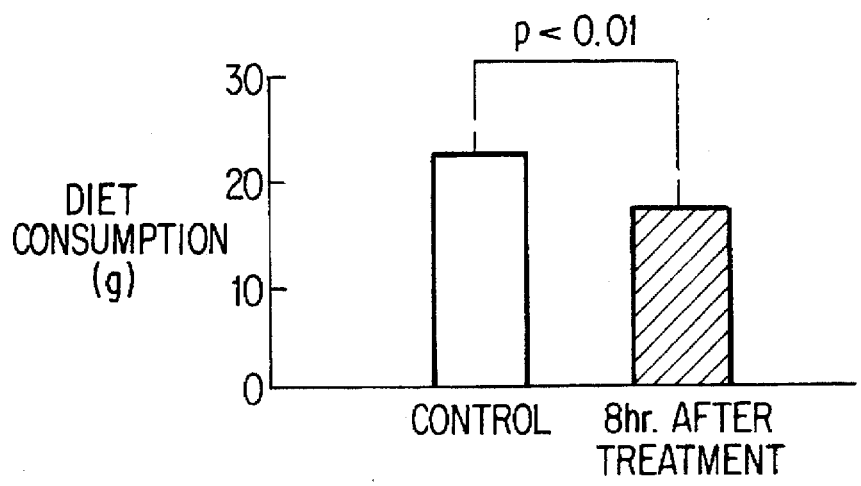
FIG. 2 shows the anorexigenic effect of aFGF intrathird ventricularly administered to rats.

FIG. 2 shows that the appetite for food in rats treated with aFGF intra third-ventricularly (220 ng/rat) decreases significantly (p<0.01 vs. control animal).

Figure 3:
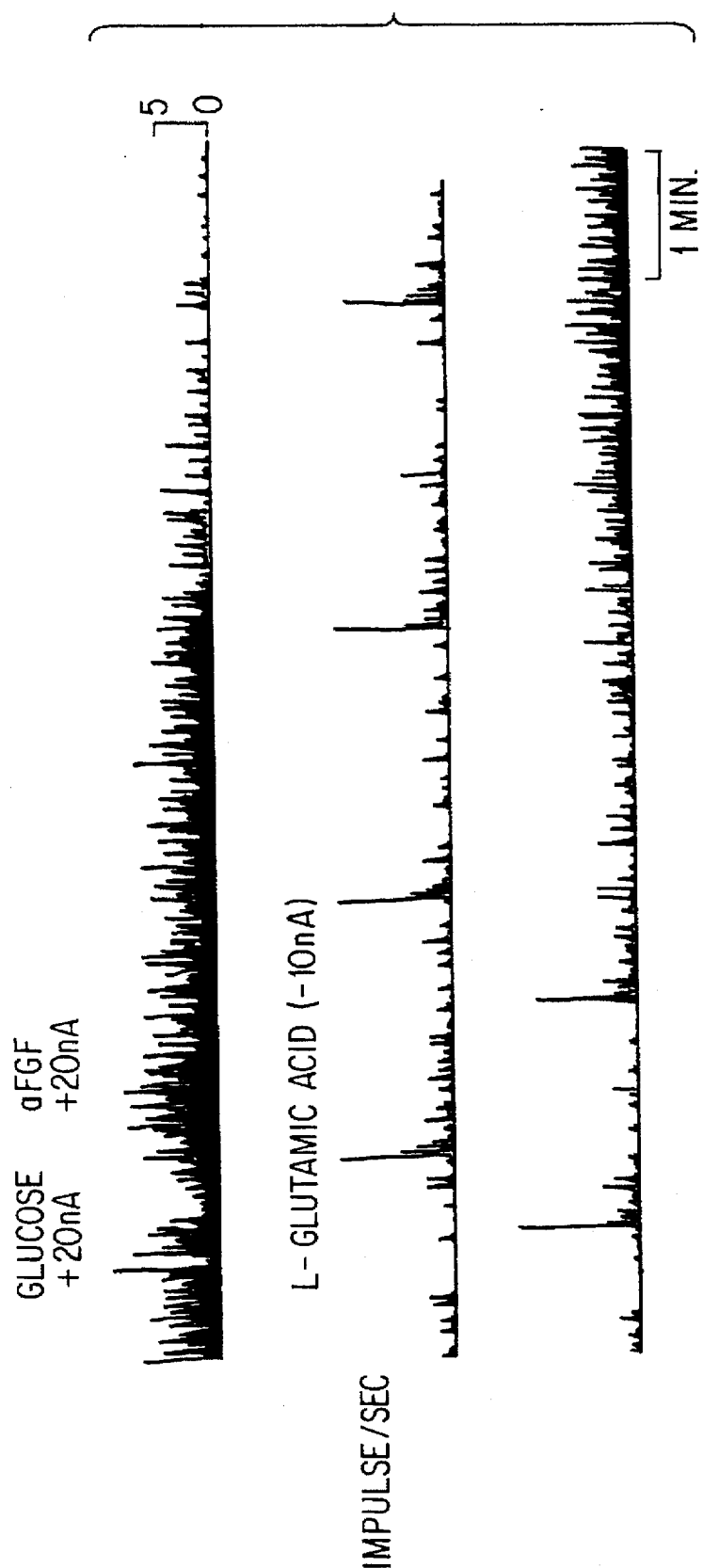
FIG. 3 shows the electrophysiological effect of aFGF on glucose-sensitive neurons in the lateral hypothalamic area (feeding center) of rats.

FIG. 3 indicates the spontaneous discharge of glucose sensitive neurons in the lateral hypothalamic area chronologically. The recording obtained is of neuron patterns iontophoretically obtained using multi-barreled microelectrodes from neurons of the lateral hypothalamic area (feeding center) of rats fed glucose, aFGF and L-glutamic acid.

The amounts of materials administered iontophoretically are indicated in FIG. 3 on the basis of nanoamperes (nA). The neuron recording pattern suggests that a latent strong suppression of neural activity occurs eight and a half minutes after aFGF treatment and continues for 15 minutes. A similar phenomenon to this pattern of aFGF treatment has been noted upon the administration of some phorbol esters such as protein-kinase C activator, i.e., 1-oleyl-2-acetyl-glycerol to a subject.

In contrast, the effects of both phorbal ester and αFGF disappear upon administration of protein-kinase C inhibitor, and imipramine (10,11-dihydro-N,N-dimethyl-5H-dibenz[b, f]axepine-5-propanamine), suggesting that the physiological function of aFGF tends to activate the protein kinase C.

Histochemical examination, using antibody for the full sequence of aFGF, indicates that the areas stained by the antibody in the brain are confined mainly to the ependymal cells during the period of hunger. However, within about 2 hours after mealtime, these areas change to other areas including the lateral hypothalamic area, zona incerta, hippocampus, amygdala and nucleus solitalis. Some ependymal cells lose intracellular aFGF, which moves into the brain parenchyma tissue. (The distribution of mRNA of aFGF in the brain ventricles and the hypothalamus are examined by an in situ hybridization technique using cDNA of aFGF from the N-terminus of this peptide sequence). The ependymal cells are positive, but the neurons of the lateral hypothalamic area are negative. These facts indicate that release of aFGF from the ependymal cell after mealtime or glucose administration is defused in either the cerebrospinal fluid or the brain parenchymal tissue and subsequently, aFGF is incorporated into the brain area, mentioned above.

This evidence strongly suggests that aFGF is either a possible component as a neurotrophic factor in the survival of neurons and maintains their function or it induces the plasticity to reconstruct the neural network by the sprouting neurite after brain ischemia and subsequent development of neuronal death.

The survival rate of the pyramidal cells in the hippocampal CA1 layer of gerbils pretreated with or without aFGF pretreatment was examined, when the short term brain ischemia was experimentally induced. Each animal had subcutaneously implanted on its back an Alzet's mini-pump containing aFGF or in ringer saline solution (20 ug/ml)(as a control). The pump or each animal was cannulated bilaterally into the lateral ventricles for the administration of aFGF (200 ng/animal/day) constantly for 7 days.

Three days after the implantation was performed, the carotid artery of each gerbil was bilaterally occluded for 5 minutes under 2% (v/v) halothane in oxygen gas. Their forebrains became ischemic and immediately anesthesia was terminated. Five minutes later the occlusion was released and the blood circulation was allowed to recover.

Each gerbil was fixed by perfusion of 2.5% glutaraldehyde in 0.1M phosphate buffer (pH 7.3) and the brain of each gerbil was removed from the carcass. The fixed brain was embedded in a paraffin, and sectioned sagittally. Each section of the brain including the hippocampus, treated with Nissl's stain, was examined histopathologically. Severe damage in the hippocampal pyramidal cells of the CA1 layer in the control animals was observed. In the other hand, no pathological changes were observed in the same area of each animal which had received treatment with aFGF constantly (Photos 3 and 4).

Figure 4:
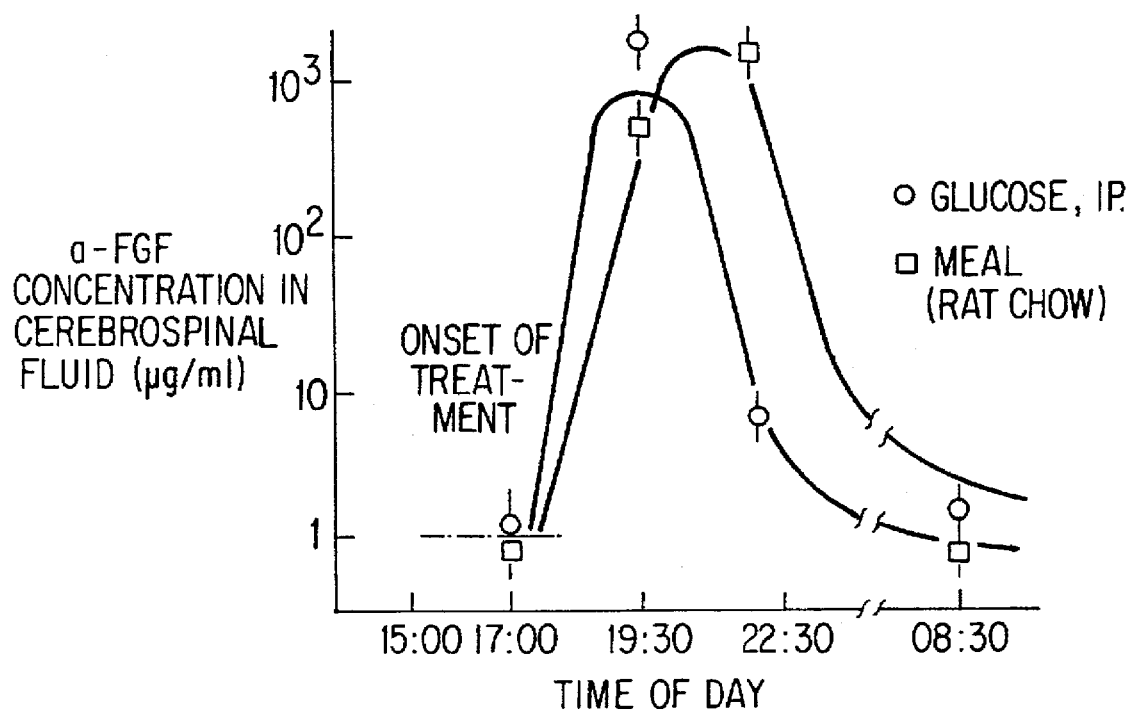
FIG. 4 shows the changes of aFGF concentration in the cerebrospinal fluid of rats fed meal (cat chow) or administered glucose intraperitoneally (29/kg body weight)
Figure 5:
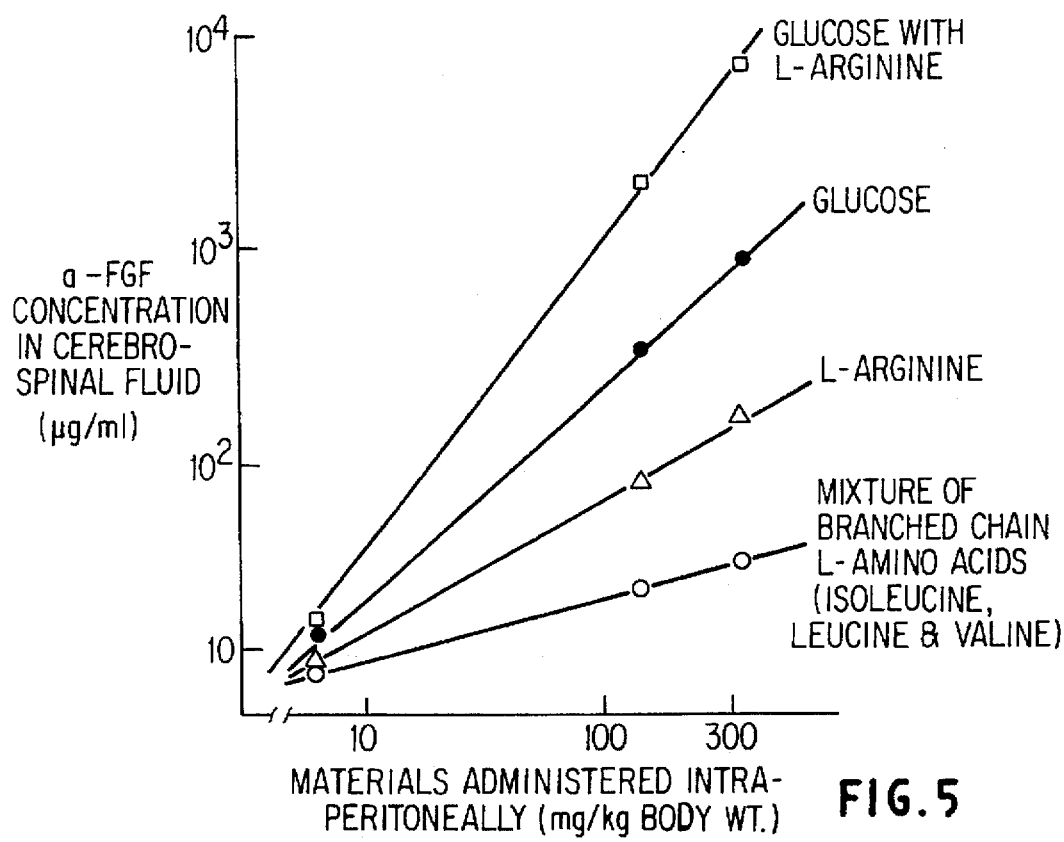
FIG. 5 shows the effects of nutrients administered intraperitoneally to rats on the aFGF concentration in the cerebrospinal fluid.

On the other hand, aFGF release into the cerebrospinal fluid was observed and reached a maximum level 2 hours later when rats were administered nutrients orally or parenterally, such as glucose, L-arginine, L-leucine, L-isoleucine or L-valine (FIGS. 4 and 5).

These facts seem to replace aFGF therapy with intravenous or enteral alimentation for patients under recovery from brain ischemia and/or hypoglycemia.

In addition, the possibility of these nutrients for patients with the disorder of memory function was examined using mice by the passive avoidance test.

Each mouse was acclimated in a specially designed cage, which was separated into a light room and a dark room. On the second day, each animal was settled in the light room of the same cage the second hour after administration of glucose with or without arginine intraperitoneally (control animal was given saline). When the mice moved to enter the dark rooms, they received a weak electric shock as an acquisition trial.

On the third day, each mouse was settled in the same fashion and the latency from the light room to the dark one was determined, as degree of memory retention. Data from the passive avoidance test are show in FIG. 6, indicating that the intraperitoneal administration of glucose with or without arginine is quite effective in enhancing memory retention. Similar effects with respect to glucose and L-arginine were also observed when an L-amino acid such as L-leucine, L-isoleucine or L-valine was administered to potent the release of aFGF in the brain. A number of facts have been accumulated which establish the discovery of a new-drug for senile dementia. The drug of the present invention for the treatment of dementia without giving rise to any adverse effects has the following composition: (1) aFGF, (2) related compounds, such as physiologically active fragments and analogue peptides, (3) nonpeptide organic chemicals with similar active domains to aFGF, and (4) nutrients with activity to release αFGF, i.e., glucose, L-arginine, L-leucine, L-isoleucine, and L-valine. Although treatment with glucose or arginine alone definitely improves the symptoms of patients exhibiting brain ischemia and subsequent dementia, the combination of glucose and L-amino acids, mentioned above, is quite effective after a subject has recovered blood flow and energy metabolism after spasms. But the continuous administration of aFGF into the brain is required while patients are under ischemic or hypoglycemic shock.

It is pointed out that aFGF is a known substance which is manufactured by culturing aFGF-yielding cells or by a recombinant DNA method using bacteria. Also, physiologically active fragments of aFGF can be produced from αFGF by enzymatic degradation or by chemical treatment. Further, peptide analogues of aFGF such as Ala-aFGF and Met-aFGF can be produced using the recombinant DNA technique.

In addition, nonpeptide organic chemicals having a physiologically active domain similar to aFGF may be employed such as the ester of a phorbol ester group as found in 1-oleyl-2-acetyl-glycerol, which compound can be chemically or enzymatically synthesized.

The administration of the present drug to patients with the senile dementia should be carefully controlled and depends upon the physiological state of energy metabolism and blood circulation, as well as the length of time after brain ischemia and hypoglycemia. For example, the constant infusion of FGF into the cerebrospinal fluid (1 to 200 ug/per person/day) should be employed in the instances where the patient is just recovering from spasms. Two days later, the therapy should be combined with the administration of nutrients parenterally or orally, i.e., glucose and/or L-amino acids (arginine, leucine, isoleucine and valine). The usual daily dose ranges from 1 to 100 g/per person/day, if possible, less than 60 g/per person/day.

The drug treatment regimen for the treatment of senile dementia can also include glucose and L-amino acids, as mentioned above. Typical drug formulations include powders, granules, tablets, sugar-coated tablets, capsules, liquids and the like. Further, the active component may be formulated as part of an intravenous formulation or as an elemental peptide alimentation. FGF and its related analogues and fragments can be constantly administered to the brain.

Having now generally described this invention, a further understanding can be obtained by reference to certain specific examples which are provided herein for purposes of illustration only and are not intended to be limiting unless otherwise specified.

[EXAMPLE 1]

Male gerbils, weighing around 250 g, were subjected to induced brain ischemia by bilateral occlusion of the carotid artery for 5 minutes. Then, the occlusion was released and the blood circulation was allowed to return to normal. Five days later the brain of each animal was fixed by the perfusion of 2.5% (v/v) glutaraldehyde in 0.1M phosphate buffer (pH 7.3) and pathological examination was performed using the sagittal section of the brain including the hippocampus with Nissl's stain. The lesion exhibiting necrosis of the pyramidal cells in the hippocampal CA1 layer was observed.

A group of similar male animals, weighing around 250 g, each had an Alzet's mini-pump (2002 type, 0.5 ul/hr.) containing aFGF (20 ug/ml) in a saline solution containing heparin (50 ug/ml) planted on their backs. The solution was administered for 7 days.

Three days after this treatment, each animal was subjected to bilateral occlusion by the carotid artery for 5 minutes under parnene anesthesia. Each animal fell into forebrain ischemia. Immediately anesthesia was discontinued. Five days after this treatment, the animals were anesthetized by pentobarbiturate, Nembtal (20 mg/kg body weight, i.p.), and their brains were fixed by perfusion with glutaraldehyde solution. The fixed brain was embedded in a paraffin and the serial sagittal sections (15 um thick) were prepared with Nissl's stain and then were examined microscopically. Control animals treated with saline instead of aFGF in the same fashion were also examined. These animals showed severe brain damage including pyramidal cell necrosis in the hippocampal CA1 layer (Photos 1 (×13,1) and 2 (×100). Nonetheless there were no lesions in the same area of brain in animals administered aFGF (Photos 3 (×13.2) and 4 (×100).

[EXAMPLE 2]

When overnight-fasted male rats, weighing 250 g (Sprague-Dawley strain) were exposed to commercial rat chow or treated with glucose intraperitoneally (2.0 g/kg body weight), the changes of aFGF concentration in the cerebrospinal fluid were determined by a bioassay using specific behavioral responses of the hydra japonica to aFGF.

The results obtained are show in FIG. 4, and suggest that the secretion of aFGF in a rat, given glucose intraperitoneally, was essentially lower and slower than the instances where the rats were fed regular meals.

In addition, the aFGF levels in rats, given glucose with or without L-arginine intraperitoneally increased at 2 hours after this treatment and a similar effect was observed in the cases of a mixture of branched chain L-amino acids, leucine, isoleucine and valine. These data are shown in FIG. 5 and indicate that these nutrients can cause the linear release of aFGF in the brain in a dose-response manner.

[EXAMPLE 3]

The anorexigenic effect of aFGF administration intra-third ventricularly to overnight-fasted rats (220 ng/rat) was examined. The treatment with aFGF reduced diet consumption significantly (FIG. 2).

When the neuronal recording from the glucose-sensitive neurons in the lateral hypothalamic area (feeding center) of conscious rats was carried out, the spontaneous discharge as a neural activity was severely suppressed by iontophoretical application of aFGF after the latency of 8.5 minutes, despite the fact that the response to glutamic acid remains unchanged (FIG. 3).

The facts are evident that aFGF is potent and strongly suppresses the activity of neurons, which respond to both glucose and glutamic acid extracellularly.

[EXAMPLE 4]

Figure 6:
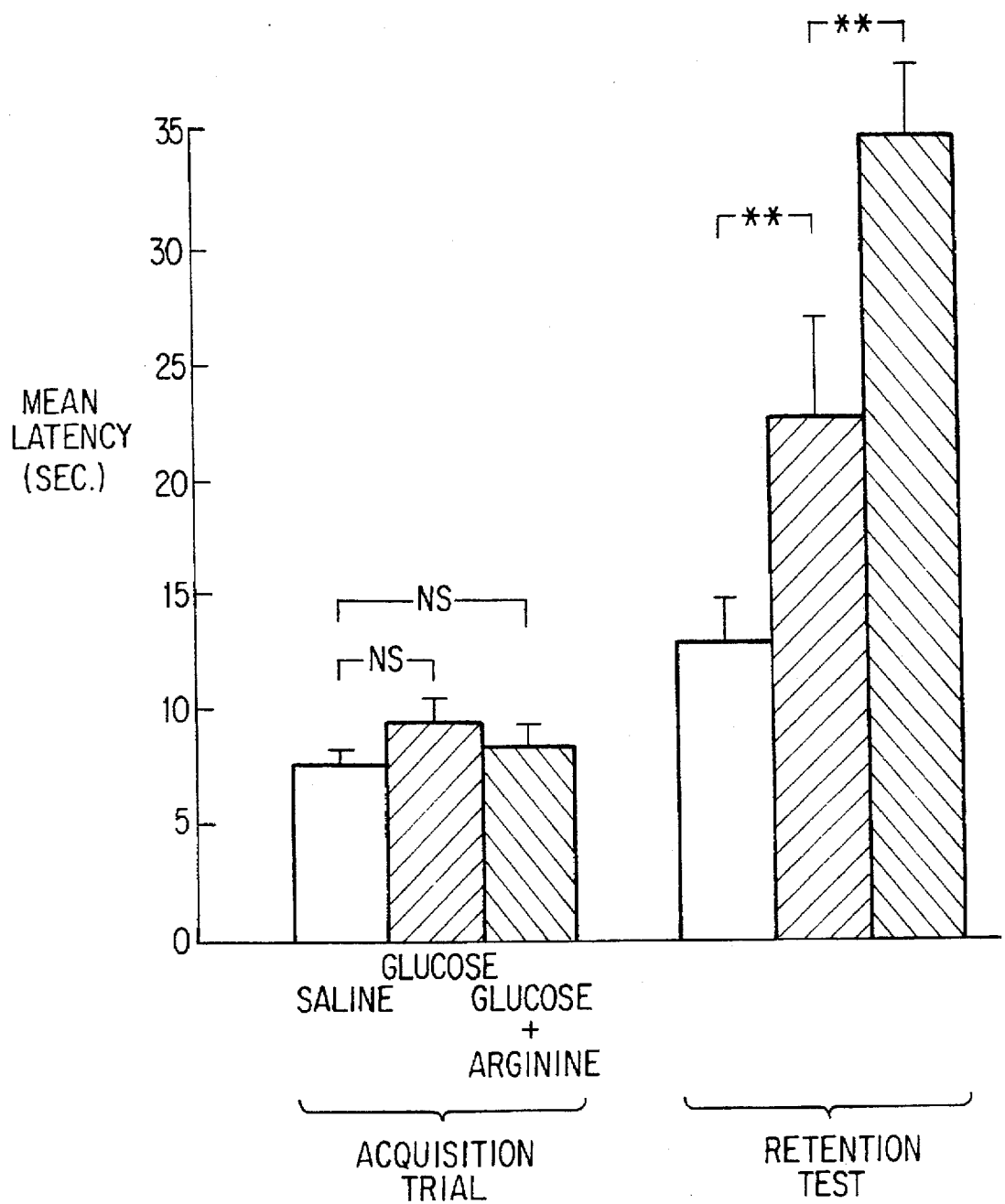
FIG. 6 shows the effect of pretreatment by intraperitoneal injection of glucose with or without L-arginine on the passive avoidance response in mice.
Figure 8:
FIGS. 8–11 are a series of photographs of the Nissl's stained sagittal section of rat brain including the hippocampus taken as described in Example 1.
Figure 9:
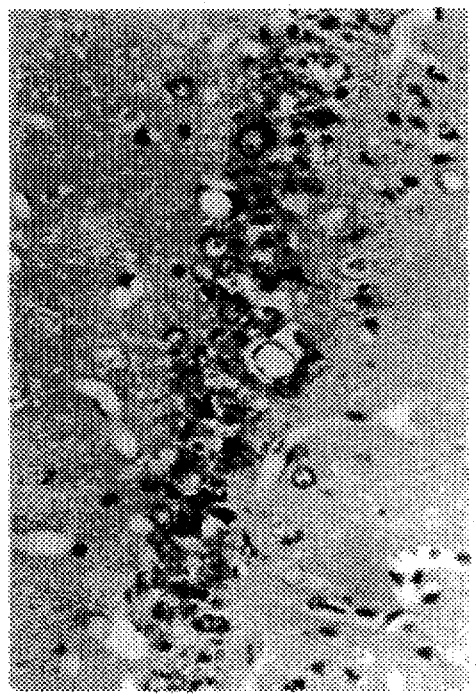
Figure 10:
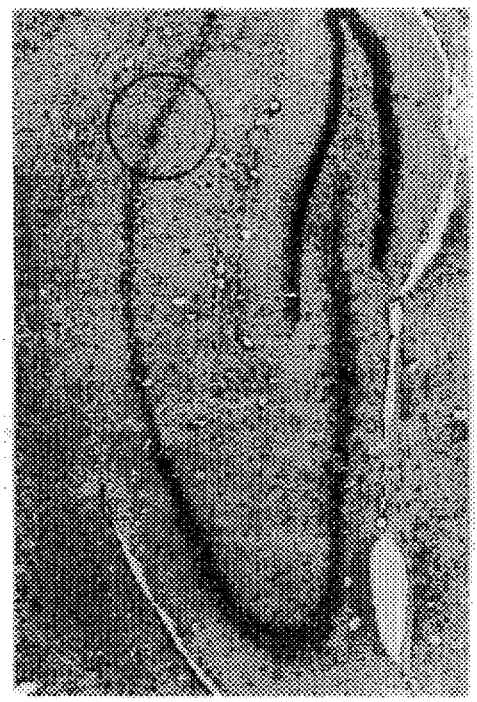
Figure 11:
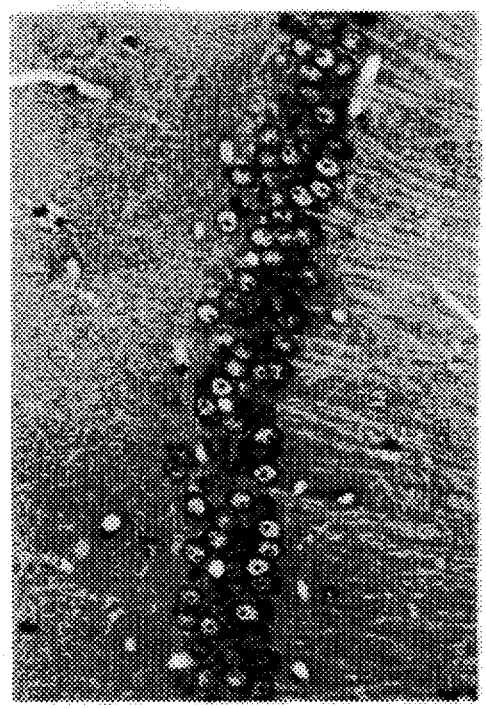

Male mice, weighing 40 g, were acclimated in specially designed cages having separate light and dark rooms. On the second day of acclimation, the animals were pretreated by the intraperitoneal administration of glucose (2 g/kg body weight) with or without L-arginine (2.1 g/kg body weight). Two hours later, they were settled in the light room in the same fashion as previously and received a weak electric shock if they attempted to enter the dark room (acquisition). On the third day, mice were settled in the light room again and the time of latency to move from the light room to the dark room was determined as a measure of memory retention for the acquisition trial (retention test). Data from this passive avoidance test are shown in FIG. 6. These data indicate that pretreatment with glucose significantly enhances memory retention in mice and that the administration of glucose concomitant with L-arginine is much more effective than that of glucose alone.

[EXAMPLE 5]

The constant administration of glucose with or without L-arginine was also examined in the exactly same fashion as aFGF treatment using similar gerbils (see [example 1]).

Figure 7:
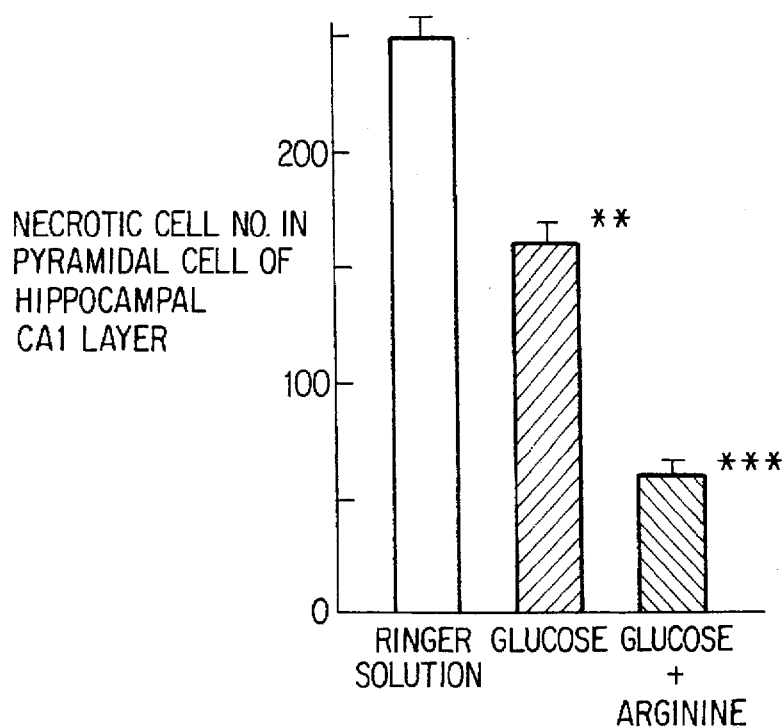
FIG. 7 shows the effect of oral administration of glucose with or without L-arginine to gerbils on the degree of necrotic pyramidal cells in the hippocampal CA1 layer after brain ischemia for 5 minutes.

The necrotic pyramidal cell number in the hippocampal CA1 layer at the same position to each other group (N=10) was counted microscopically. The yield data are shown in FIG. 7, and indicate that the treatment with glucose improved the survival rate of the pyramidal cells after the short term brain ischemia (p<0.01 vs. saline control) and the concomitant administration with L-arginine was more effective than the case of treatment with glucose alone (p<0.01 vs. glucose alone, p,0.001 vs. saline control).

[Efficacy of present invention]

The drug which is used in the invention for the treatment of senile dementia is composed of aFGF, its related materials and optionally some nutrients which have the activity of aFGF such as L-arginine.

This drug of the present invention is effective in patients with spasms of both ischemia and hypoglycemia in the brain by reason that the neurons with sensitivity for glutamic and/or aspartic acid tolerate the tremendously increased amounts of extracellular glutamic and/or aspartic acids. Thus, the consequent neuronal death and the development of dementia after the spasms are prevented.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A method of treating a subject suffering from ischemic shock, comprising:

administering to said subject from 1 to 200 µg/person/day of α-FGF as the active ingredient of a pharmaceutical composition further containing a pharmaceutically acceptable carrier.

2. The method of claim 1, wherein the composition of claim 1 is administered by intravenous feeding.

3. The method of claim 1, wherein the composition of claim 1 is administered by the alimentary tract.

4. A method of treating a subject suffering from ischemic shock, comprising:

administering to said subject a therapeutically effective amount of α-FGF and glucose.

5. The method of claim 4, wherein said subject is further administered a L-amino acid.

* * * * *